(12) United States Patent
Mehdizade

(10) Patent No.: US 8,529,570 B2
(45) Date of Patent: Sep. 10, 2013

(54) TECHNIQUE AND DEVICE FOR LAMINAR OSTEOTOMY AND LAMINOPLASTY

(75) Inventor: Amir Mehdizade, Geneva (CH)

(73) Assignee: The Adelman Research Ltd, Mahe (SC)

( * ) Notice: Subject to any disclaimer, the term of this patent is extended or adjusted under 35 U.S.C. 154(b) by 519 days.

(21) Appl. No.: 12/519,297

(22) PCT Filed: Dec. 14, 2007

(86) PCT No.: PCT/IB2007/004560
§ 371 (c)(1),
(2), (4) Date: Jun. 15, 2009

(87) PCT Pub. No.: WO2008/139260
PCT Pub. Date: Nov. 20, 2008

(65) Prior Publication Data
US 2010/0114100 A1    May 6, 2010

Related U.S. Application Data

(60) Provisional application No. 60/874,970, filed on Dec. 15, 2006, provisional application No. 60/963,310, filed on Aug. 3, 2007.

(51) Int. Cl.
*A61B 17/70*    (2006.01)

(52) U.S. Cl.
USPC .......................... 606/86 A; 606/96; 606/104

(58) Field of Classification Search
USPC .......................... 606/86 A, 96, 104; 600/235
See application file for complete search history.

(56) References Cited

U.S. PATENT DOCUMENTS

| | | | | |
|---|---|---|---|---|
| 4,649,919 A * | 3/1987 | Thimsen et al. | ................. | 606/80 |
| 5,772,661 A * | 6/1998 | Michelson | ................. | 606/86 A |
| 6,358,254 B1 | 3/2002 | Anderson | | |
| 7,166,107 B2 | 1/2007 | Anderson | | |
| 2005/0080418 A1* | 4/2005 | Simonson et al. | ............... | 606/61 |
| 2005/0216002 A1* | 9/2005 | Simonson | ...................... | 606/61 |
| 2005/0234425 A1 | 10/2005 | Miller et al. | | |
| 2006/0195102 A1 | 8/2006 | Malandain | | |
| 2007/0219555 A1 | 9/2007 | Anderson | | |
| 2007/0276370 A1 | 11/2007 | Altarac et al. | | |

FOREIGN PATENT DOCUMENTS
WO       02/096294 A2    12/2002

OTHER PUBLICATIONS
International Search Report for PCT/IB2007/004560.

* cited by examiner

*Primary Examiner* — Andrew Yang
(74) *Attorney, Agent, or Firm* — Brooks Kushman P.C.

(57) ABSTRACT

This invention relates to a technique for performing laminar osteotomy (dividing of the spinal lamina, a posterior structure of vertebra). The term osteotomy is derived from os (bone), tomy (to cut or remove), and laminoplasty (the reshaping of the lamina). This technique can be performed with or without visual assistance such as cameras used with endoscopy, or image guidance such as fluoroscopy, computer tomography (CT) or magnetic resonance imaging (MRI).

16 Claims, 23 Drawing Sheets

TECHNIQUE AND DEVICE FOR LAMINAR OSTEOTOMY AND LAMINOPLASTY

CROSS-REFERENCE TO RELATED APPLICATION

This application is a U.S. national phase of PCT Appln. No. PCT/IB2007/004560 filed Dec. 14, 2007, which claims the benefit of U.S. Provisional Application Ser. No. 60/874,970 filed Dec. 15, 2006 and U.S. Provisional Application Ser. No. 60/963,310 filed Aug. 3, 2007, each of which applications are expressly incorporated herein by reference in their entirety.

BACKGROUND OF THE INVENTION

1. Field of the Invention

The invention relates to a minimally invasive surgery (MIS) technique and devices for performing laminar osteotomy and laminoplasty; with or without visual or image assistance such as cameras used with endoscopy, fluoroscopy, CT, or MRI.

2. Related Art

Spinal stenosis is a condition characterized by a narrowing of the central spinal canal or inter vertebral foramen. Spinal stenosis results in back and leg pain due to the compression of spinal nerves. Severe cases of spinal stenosis require spinal decompressive laminectomy surgery or spinal laminoplasty surgery to enlarge the spinal canal and relieve pressure on the neuronal elements. These neuronal elements consist of the spinal cord, conus medullaris, nerve roots, and all other structures covered by the dura mater (a connective tissue membrane covering the neuronal elements). Pressure on the neuronal elements is relieved by removing or reshaping, in part or completely, structures that are the source of compression, which may include bone or soft tissues (ligaments, joint capsule, and other non-bone structures).

Spinal stenosis is considered primary (congenital) or secondary (acquired). Isolated primary spinal stenosis is very uncommon and involves spinal canal narrowing caused by a congenital abnormality or a disorder in development. Secondary stenosis usually results from degenerative changes.

Decompressive laminectomy is the standard surgical procedure for patients with spinal stenosis, when non-surgical treatments have failed. The surgery is traditionally accomplished via a posterior approach, with the patient prone under general anesthesia. In the posterior approach, after a sterile field is established, a longitudinal incision is made along the midline posteriorly at the level of the stenosis. The incision is carried down to the posterior elements identifying the spinous process, the lamina, and the facet joints. An X-ray or other fluoroscopic image is usually obtained with a radio-opaque marker to ensure that the correct spinal level has been exposed. The musculotendonous attachments to the posterior elements are systematically removed to expose the vertebral anatomy. The facet joints may be partially or completely removed based on the pathology that is present. Removal of a significant part or the entire facet joints will result in spinal instability. In such cases, a spinal fusion is typically required to stabilize the spine.

Another surgical method to create additional room in the spinal canal is called a laminoplasty. In this technique the lamina is divided, spread apart, and a bone graft is to inserted to enlarge the space available for the neuronal elements. Laminoplasty can be performed using unilateral or open door laminoplasty. In unilateral or open door laminoplasty, the lamina of one side of the vertebra is divided completely, while the other side is partially cut to create a hinge. The vertebral posterior element is then rotated about the hinge, and a graft is inserted into the opening, increasing the spinal canal space. Another laminoplasty procedure is called the bilateral or French door laminoplasty in which the spinous process (where the lamina meet in the posterior midline) is divided completely. Each lamina on either side of the posterior midline is then cut half way through, creating two hinges. The separated posterior elements are then opened at the cut spinous process, and a graft is inserted into the opening, again increasing the opening of the spinal canal.

Traditionally, laminectomies and laminoplasties are open surgical procedures resulting in extensive recovery times for patients and increased costs and risks of complications. Thus, there has been a demand for MIS techniques and tools to perform laminectomies and laminoplasties. Further, MIS techniques are becoming more widespread in the surgical subspecialties. Standard open surgical procedures are being modified to become less invasive, with the goal of decreased recovery times, lessened morbidity, and cost savings. For example, novel tools and visualization techniques are being used to perform the same surgery through smaller incisions decreasing the recovery times and risks for patients. Other MIS methods, such as the present invention described herein, attempt to achieve the same result through an entirely new approach.

A variety of different surgical techniques, including laminotomy, laminectomy, and laminoplasty, have been reported for treatment of spinal stenosis. These techniques all rely on either visualization of the anatomical structures either directly or with the use of visual and imaging aids such as cameras, or fluoroscopic or plain X-ray assisted techniques. These procedures are performed using techniques that "rongeur" (French verb to nibble or piece-wise remove) the lamina to remove or reshape it. Other techniques describe burring or scraping of the bone. These methods, however, are all performed by removing the bone from the anterior-posterior axis of the lamina 9, perpendicular to the longitudinal axis of the lamina 8 (see FIGS. 1A and 2A).

In U.S. Pat. No. 6,358,254, Anderson discloses a method for performing spinal surgery in the lumbar vertebrae to alleviate spinal stenosis, wherein the vertebra is cut at the pedicle in at least one location, the portion of the cut vertebra posterior to the facet joint is separated from the vertebral body to expand the spinal canal, and the separated portion is secured to the vertebral body by mechanical means to allow the vertebra to heal. In U.S. Pat. No. 7,166,107 and U.S. application Ser. No. 11/656,790 (published as 20070219555), Anderson discloses a method for expanding the lumbar spinal canal by drilling a passage into a lumbar vertebra and inserting a side-cutting instrument to make the pedicle cut from within the drill hole. The separated portion is again secured to the vertebral body by mechanical means to allow healing as well as to allow the secured vertebral structure to regain its load-bearing function.

Known techniques and instruments, however, do not provide a method to ensure accurate and safe dividing of the lamina while minimizing the risk of damaging any neuronal elements. In particular, the methods described by Anderson are only suitable for use in the lumbar spine, where there is little or no risk of damage to the spinal cord or vertebral artery as is the case in the cervical or thoracic spine In view of the above, one aspect of the present invention relates to a method and device to divide the lamina in the sagittal or oblique sagittal plane 8, directed in the approximate longitudinal axis of the lamina, with the dividing instrument directed either toward the head (cephalad) or toward the tailbone (caudate). This method of dividing the lamina has not heretofore been described in open or image guided methodology. To perform this method of dividing the lamina, one aspect of the invention involves a novel guard that is inserted through the inter laminar space protecting the para-laminar structures including the neuronal elements. The guard acts to precisely guide the division of the bone while minimizing risk of injury to the neuronal elements. Furthermore, the division, cutting, drilling, burring or other techniques for removing or dividing bone compressing the neuronal elements can be done under CT scan, X-ray, fluoroscopy, MRI, or other image guidance technology to guide the division. Additionally, a surgically implantable device designed to prevent anterior translation of the divided posterior elements by means of increasing the width of the divided posterior laminar segment or decreasing the width of the divided laminar segment overlaying the central canal is disclosed (see FIGS. 7A, 7B, and 9).

SUMMARY OF THE INVENTION

One aspect of the invention described herein is an approach for performing a laminar osteotomy (laminectomy) and laminoplasty procedure that can be performed using open surgical technique or MIS techniques with or without image guidance using fluoroscopy, CT scan, X-ray, MRI, or other image technology. Advantageously, this technique may be used to treat the cervical, thoracic, or lumbar spine regions on any vertebrate.

Uniquely, when this procedure is used in conjunction with CT or MRI guidance, it allows for identifying and measuring the relevant anatomy in three dimensions, including the laminar bone distance from the skin, the thickness and depth of the lamina, height of the vertebral arch, the area of the spinal canal, and the angle of advancement and location of the skin incision for the entry point. Further, it also allows for identification of anatomical structures at risk for injury during the procedure and assessment of the relative safety of the procedure being performed.

In one aspect of the present invention, a method for performing a laminoplasty or laminar osteotomy in the sagittal or oblique sagittal plane, directed in the longitudinal axis of the lamina with a dividing instrument is introduced. In the method, one identifies a section of at least one lamina to be divided, places a guard proximate to the section of lamina to be divided, and divides the lamina. The guard protects a patient's sublaminar thecal sac and pari-laminar soft tissues structures. The guard also guides the dividing instrument through the lamina.

In another aspect of the present invention, a device is introduced which protects a patient's sublaminar thecal sac and pari-laminar soft tissue structures while procedures on the spinal lamina of the patient are performed. The device is placed parallel to the longitudinal axis of the lamina and proximate to the lamina. The device has a sub-laminar wall and a supra-laminar wall having curved or angled leading tips to allow the patient's lamina to be separated from the overlaying and underlying tissues. The supra- and sub-laminar walls are part of a cannulate cylinder allowing access to the lamina with surgical tools or a placement of devices, medications, or other therapeutic agents.

In yet another aspect of the present invention, a surgically implantable device is introduced. The device is placed on either divided edge of a patient's lamina whether unilaterally or bilaterally. The device blocks anterior translation or rotation of the divided posterior spinal elements after laminar osteotomy.

In another aspect of the invention, a method is introduced for performing a laminectomy or laminoplasty spinal procedure using fluoroscopic, CT, MRI, ultrasound, or X-ray guidance. The method involves identifying a location for making an incision in a patient's skin; advancing a guide wire through soft tissues down to the bone under guidance; inserting and placing a device through the incision and along the path of the guide wire so that the device is proximate to the lamina to protect a patient's sublaminar thecal sac and pari-laminar soft tissue structures. The device has a sub-laminar and a supra-laminar wall having curved or angled leading tips to allow the patient's lamina to be separated from the overlaying and underlaying tissues wherein the supra- and sub-laminar walls are part of a cannulate cylinder. Then the method discloses inserting a saw, drill, burr or other lamina dividing mechanism through the cannulate cylinder of the device to the lamina to divide the lamina completely, or partially modify its shape.

BRIEF DESCRIPTION OF THE DRAWINGS

Further objects, features and advantages of various aspect of the invention will become apparent from the following detailed description taken in conjunction with the accompanying figures showing illustrative embodiments of the invention. The invention, however, is not limited to the precise arrangements and instrumentalities depicted in the figures. In the figures.

DETAILED DESCRIPTION OF THE PREFERRED EMBODIMENTS

Preferred embodiments, methods and aspects of surgical implantable devices to be used in dividing of the spinal lamina and elevation of the posterior wall of the spinal central canal are described in this section. This reshaping of the lamina, or laminoplasty results in the creation of more space for the neuronal elements in the spinal central canal. This method is of particular benefit since it can be performed through a small incision under CT, MRI, or other image guidance. Furthermore, the technique can be applied to the cervical, thoracic, and lumbar levels of the spine of any vertebrate.

Figure 1A:
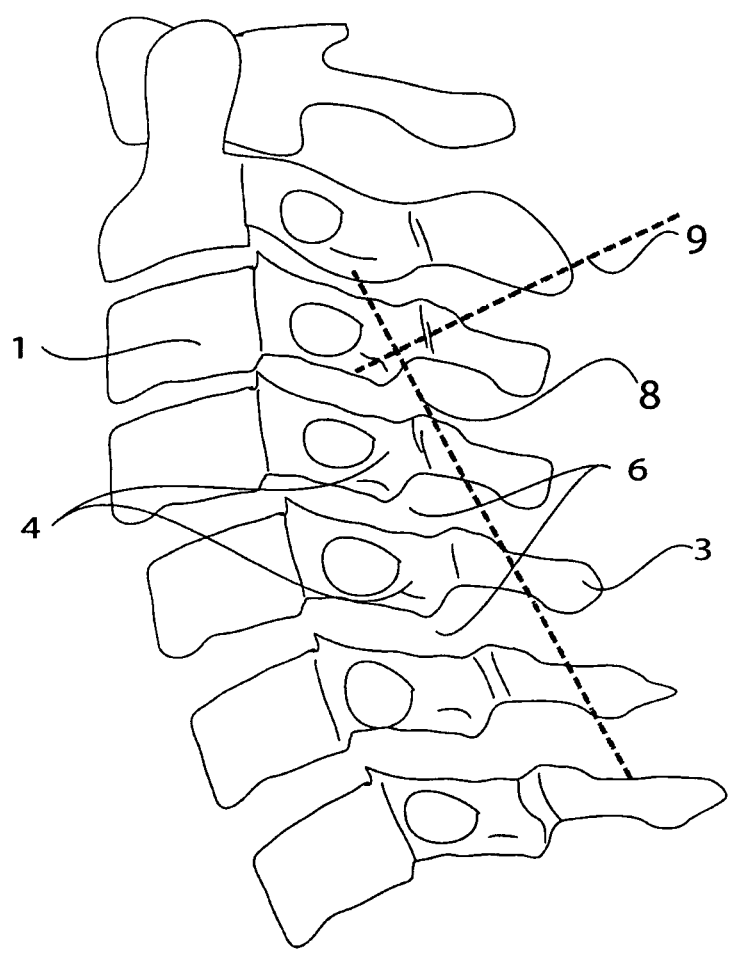
FIGS. 1A, 1B and 1C illustrate the lateral, posterior, and axial views of the cervical spine with anatomical sites labeled.
Figure 1B:
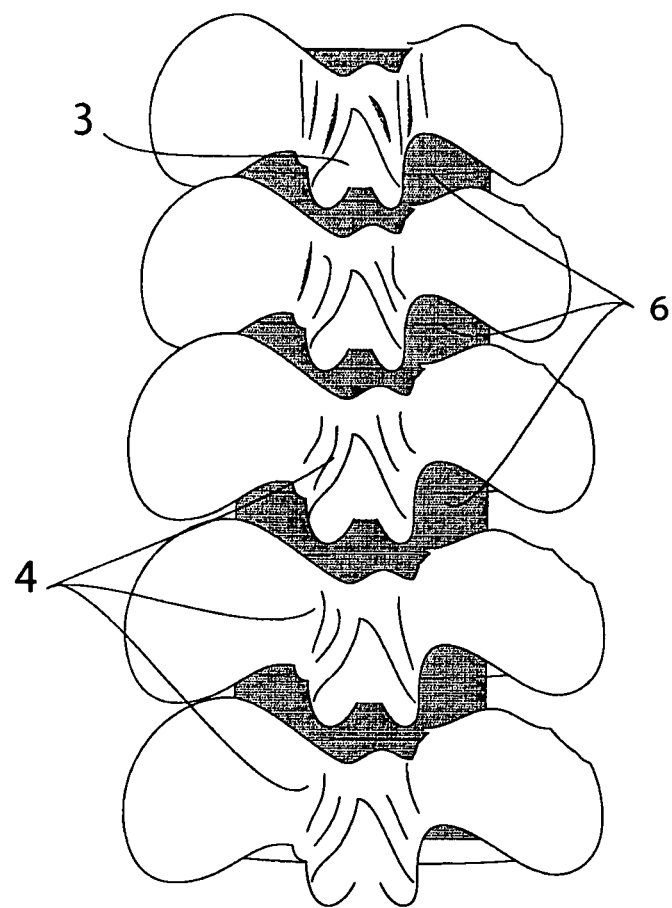
Figure 1C:
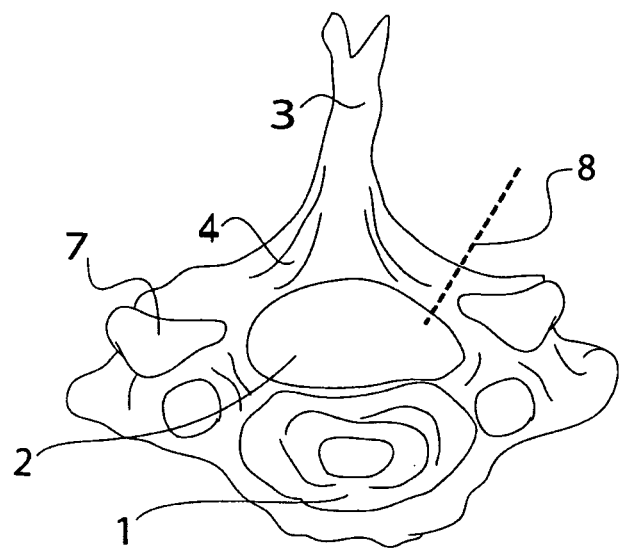
Figure 2A:
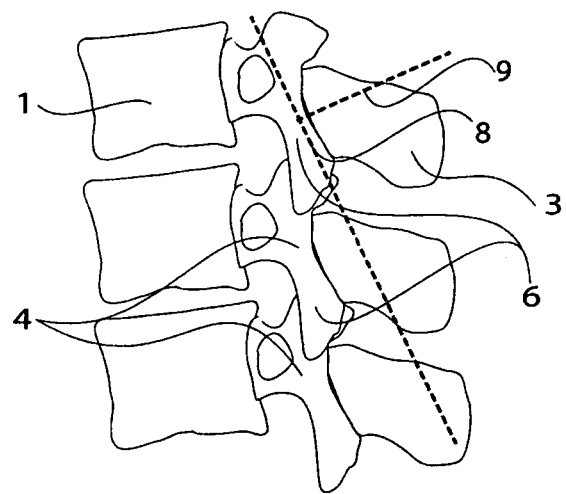
FIGS. 2A, 2B and 2C illustrate the lateral, posterior, and axial views of the lumbar spine with anatomical sites labeled.
Figure 2B:
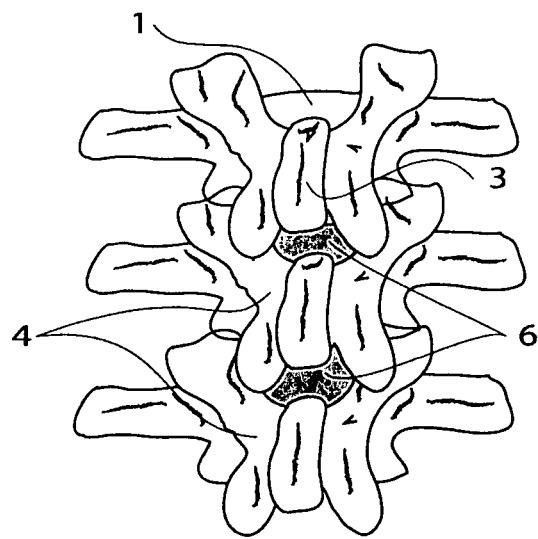
Figure 2C:
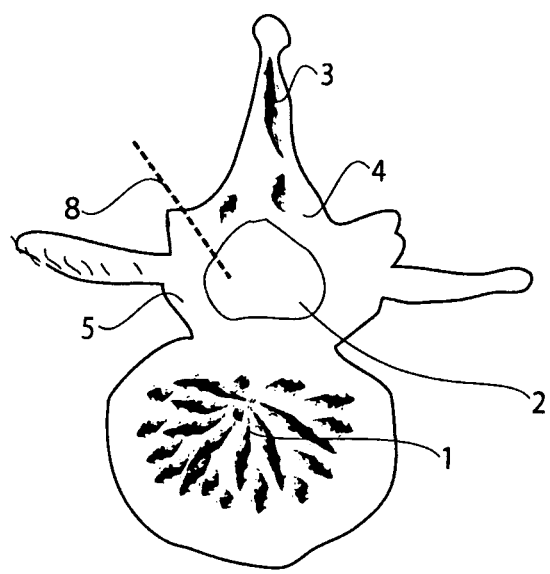
Figure 3:
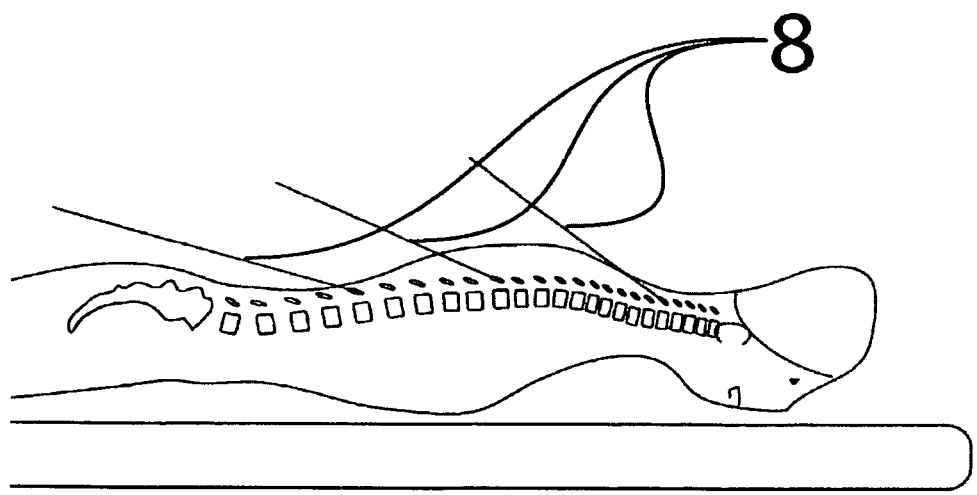
FIG. 3 illustrates a patient lying prone with the longitudinal axes of the cervical, thoracic, and lumbar lamina drawn.

FIGS. 1-2 show lateral, posterior, and axial views of cervical and lumbar vertebrae respectively. Thoracic vertebra are not drawn as they are similar in the anatomical region relevant to this description. The vertebral bodies 1 create the anterior wall of the central canal 2. The spinous process 3 is a midline bony prominence where the lamina 4 meet. This process elevates the divided posterior elements of the vertebra, effectively expanding the central canal's posterior margin or "raising the roof" of the vertebra. Pedicles 5 extend anteriorly from the lamina and create the side wall of the central canal. The inter laminar space 6 is the space between adjacent lamina that is covered by a soft tissue structure called the ligamentum flavum. The facet joints 7 are joints that connect the vertebra posteriorly. The longitudinal 8 and perpendicular 9 axes of the spinal lamina are shown in FIGS. 1 and 2. FIG. 3 further demonstrates the longitudinal axes of the lamina for the different vertebra in the cervical, thoracic, and lumbar regions on patient 10 laying prone on a procedure table 11.

This longitudinal laminar axis determines the angle at which the lamina is approached and the location of the skin incision to reach the target lamina. The patient (10) is positioned prone, lateral, or semi (sloppy) lateral on the procedure table. If performed open, or with fluoroscopic techniques, the procedure may occur in the operating room. If performed using CT or MRI guidance technologies, it may done in a scanning room or in an operating room specifically equipped with such scanning equipment. General anesthesia or sedation with local anesthesia may be used. A myelogram may be performed just prior to the procedure to allow for better visualization of the neuronal elements. This procedure may also be performed with neuronal monitoring.

The procedures performed according to the invention benefit acquired pathologies such as disk herniation, compression fractures, facet joint or ligamentum flavum hypertrophy as well as congenital pathologies such as short pedicles or central canal stenosis.

Figure 4:
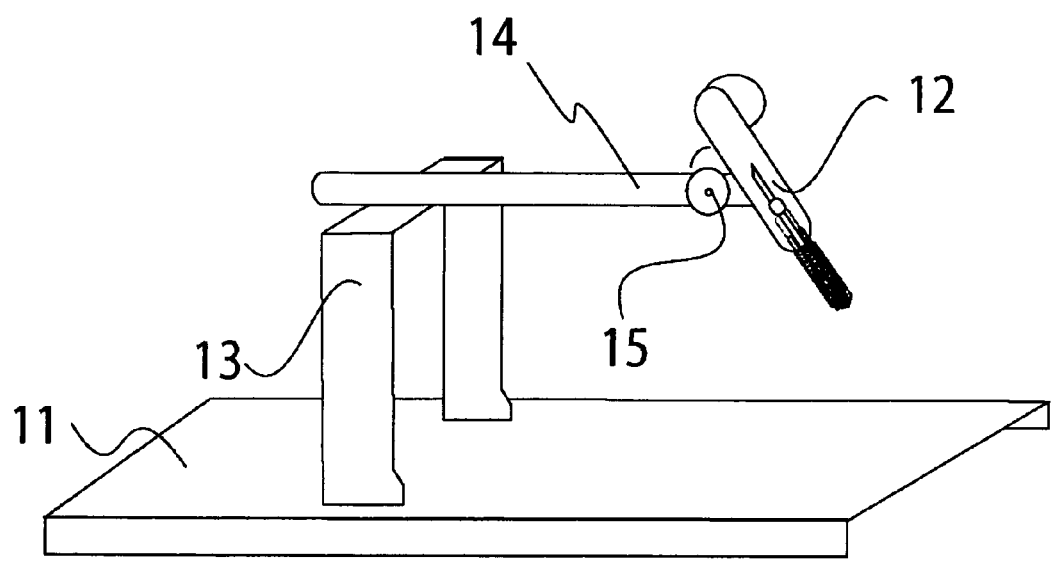
FIG. 4 illustrates a device according to one embodiment of the invention assembled on the CT scanner table with different parts.
Figure 5A:
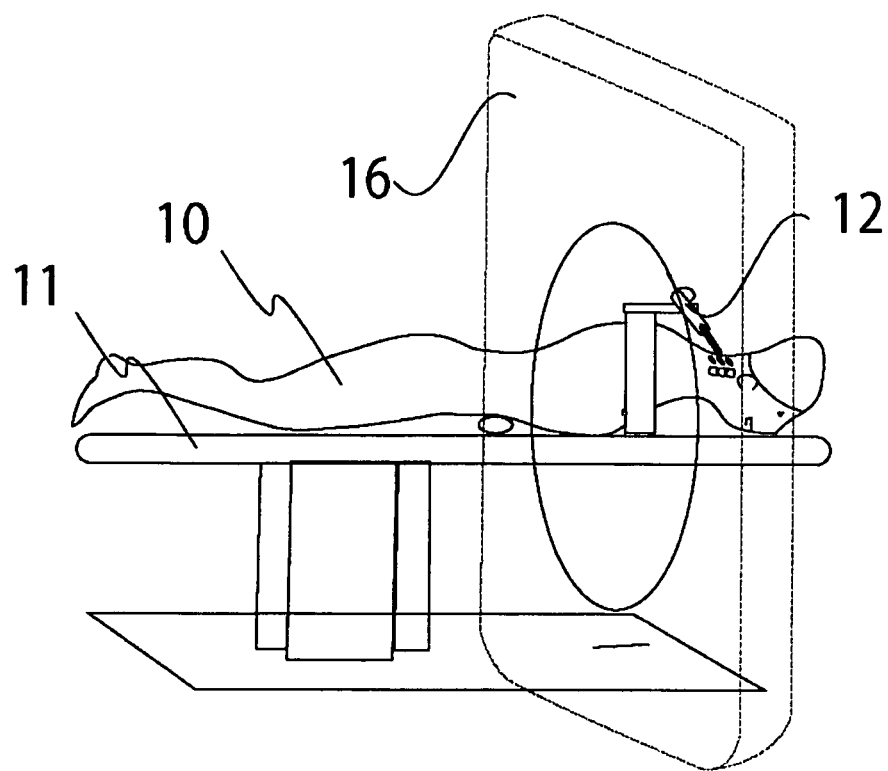
FIG. 5A is a diagram of the CT scanner, with the patient in the prone position, and a device according to the invention lined up with the patient's cervical spine.
Figure 5B:
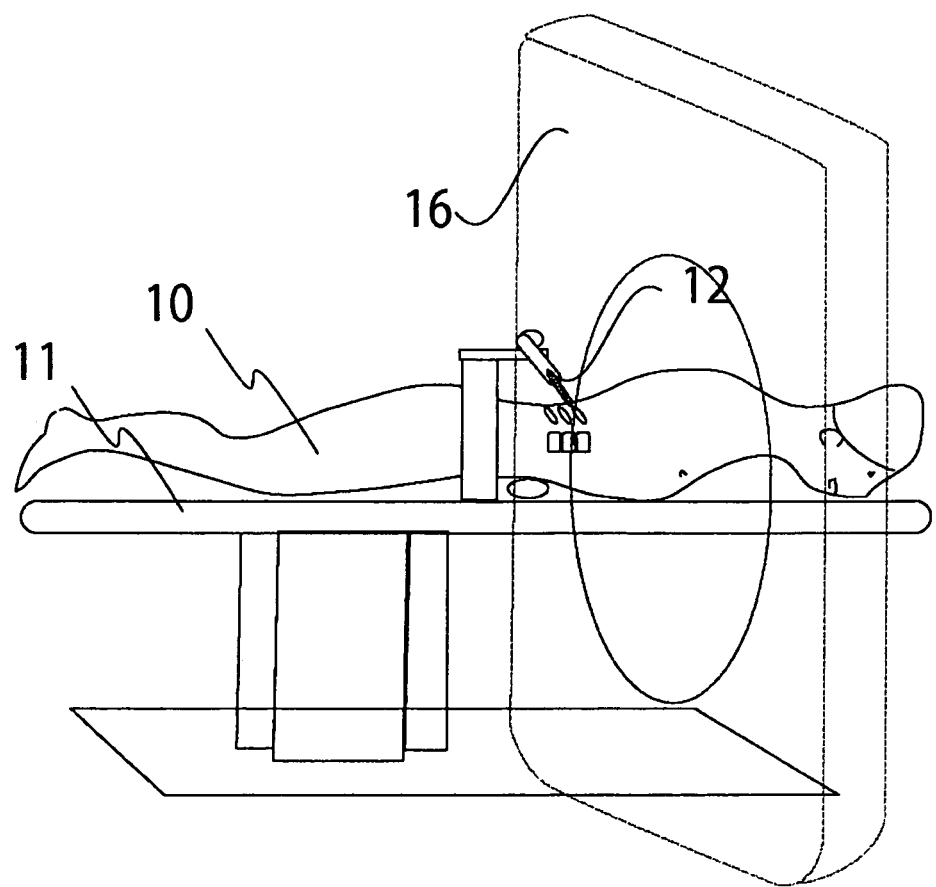
FIG. 5B is a diagram of the CT scanner, with the patient in the prone position, and a device according to the invention lined up with the patient's lumbar spine.
Figure 5C:
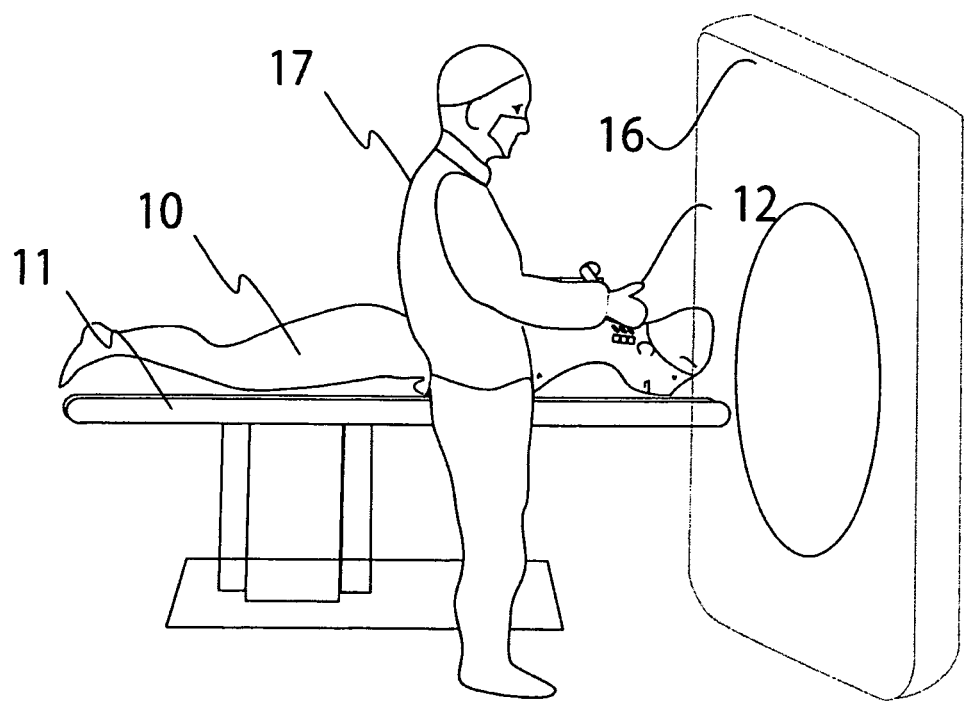
FIG. 5C is a diagram of the CT scanner, with the patient in the prone position, and an operator standing in position.
Figure 5D:
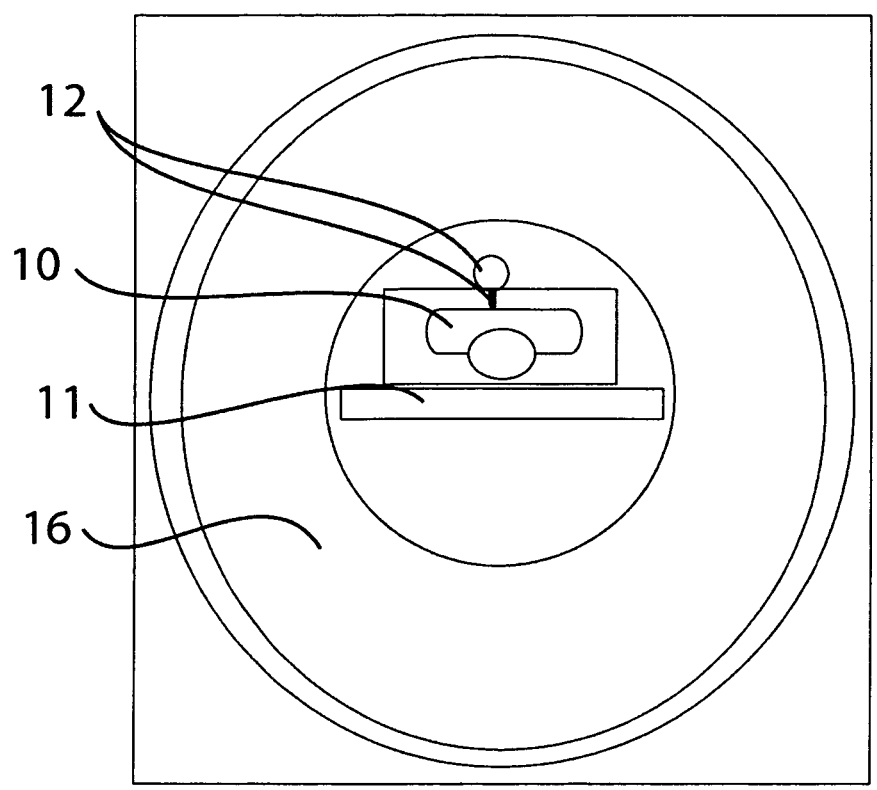
FIG. 5D is an axial diagram of the CT scanner, with the patient in the prone to position.

One embodiment of the invention is illustrated in FIG. 4. The laminar dividing mechanism 12 consists of a stand 13 that attaches to the procedure table 11. This can be a single attachment to one side of the procedure table or an attachment to both sides of the table for added stability. The stand has an arm 14 fitted with a universal joint 15 that can position the instruments used to perform the procedure and hold them stable while imaging is being performed. Control of the laminar dividing mechanism may occur robotically or otherwise with the aid of a computer or manually. Alternatively these methods and instruments can be used without the instrument stabilizing apparatus, as a free hand technique.

Another embodiment of the invention is illustrated in FIG. 5. FIG. 5A demonstrates the patient in prone position, with the device lined up to perform the procedure on the patient's cervical spine. In a preferred method according to one embodiment of the invention, a CT scanner 16 is shown, however MRI or other imaging techniques can be used. FIG. 5B shows the patient in the prone position. Here the device is lined up with the patient's lumbar spine. The procedure can also be performed on the thoracic spine. The operator 17 is shown in position performing the procedure on the cervical spine in FIG. 5C. An axial view of the patient and CT scanner is shown in FIG. 5D.

Figure 6A:
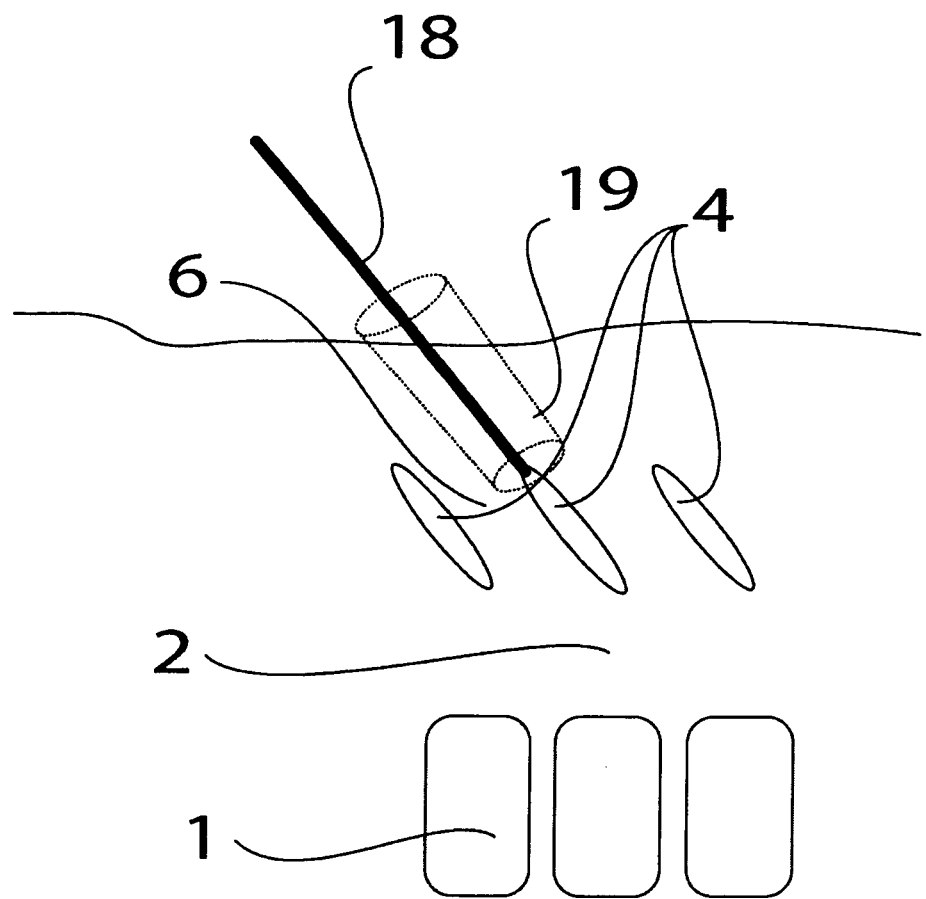
FIG. 6A is a lateral view of the patient showing the lamina exposed after incision into the patient's back along the longitudinal axis of the lamina. A dilator is placed into the incision up to the lamina. A guide wire is placed through the dilator to guide a lamina dividing mechanism to the lamina.

After achievement of a sterile field, the standard posterior surgical approach to the spine is made if an open technique is used. If image guidance is used, initial images are obtained. Since both the open and image guided techniques are a variation of one another, further description will be focused on the use of the CT scanner for the described method. The level of spinal pathology is identified with the CT scanner. Using a trajectory line through the longitudinal axis of the inferior laminar border, the site of the skin incision is identified. After making the skin incision, a blunt tip guide wire (18) is passed in line with the determined trajectory to the inferior (caudal) border of the lamina (FIG. 6A). Although this procedure can be performed from both the caudal to cranial direction as well as the cranial to caudal direction, the herein described method will be from the caudal to cranial direction.

Figure 6B:
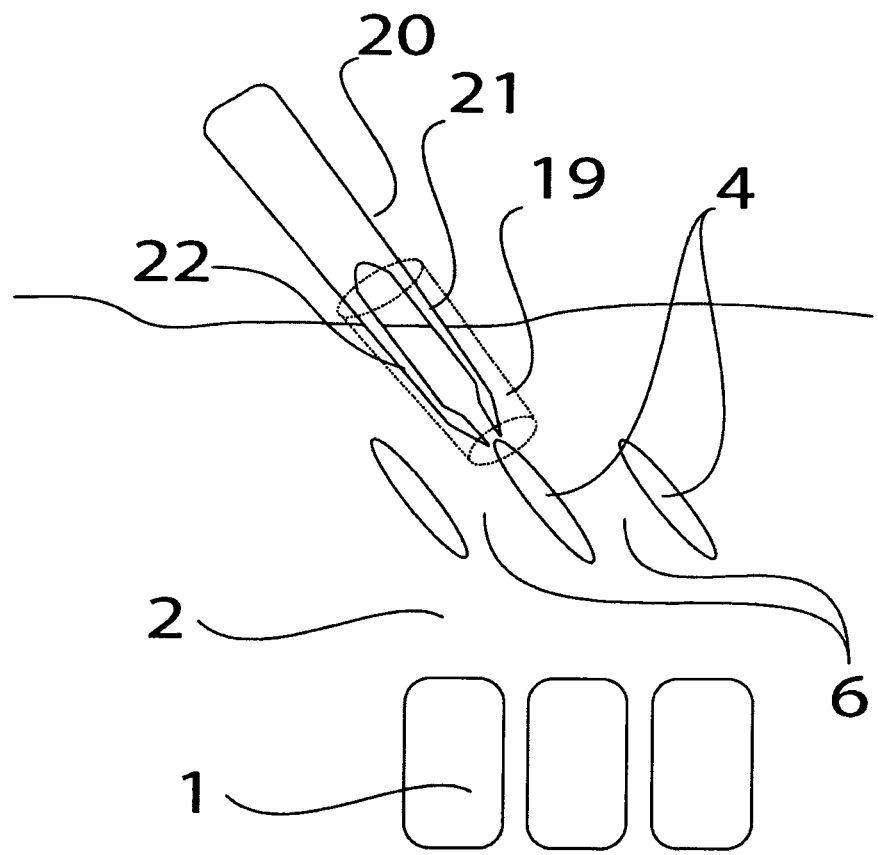
FIG. 6B is a lateral view of the patient showing the laminar guards being advanced toward the lamina in the dilator tube along the longitudinal axis of the lamina.
Figure 6C:
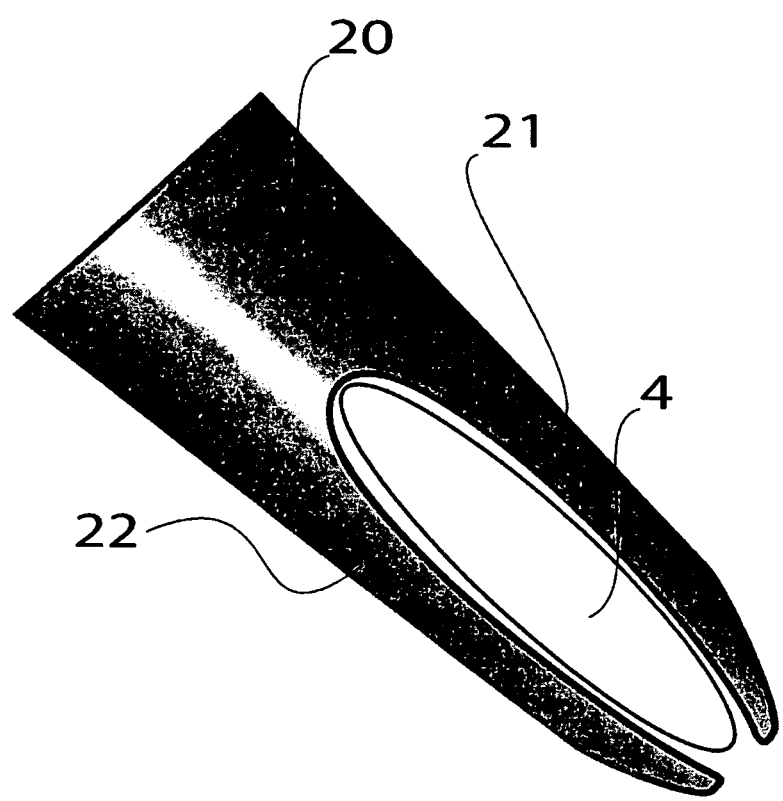
FIG. 6C is an enlarged view of the lamina with the laminar guards fully advanced, demonstrating the safety stop preventing the advancement of the laminar guards into the spinal canal. The length of the laminar guard sides act as a safety to prevent over advancement of the laminar guard into the spinal central canal.
Figure 6D:
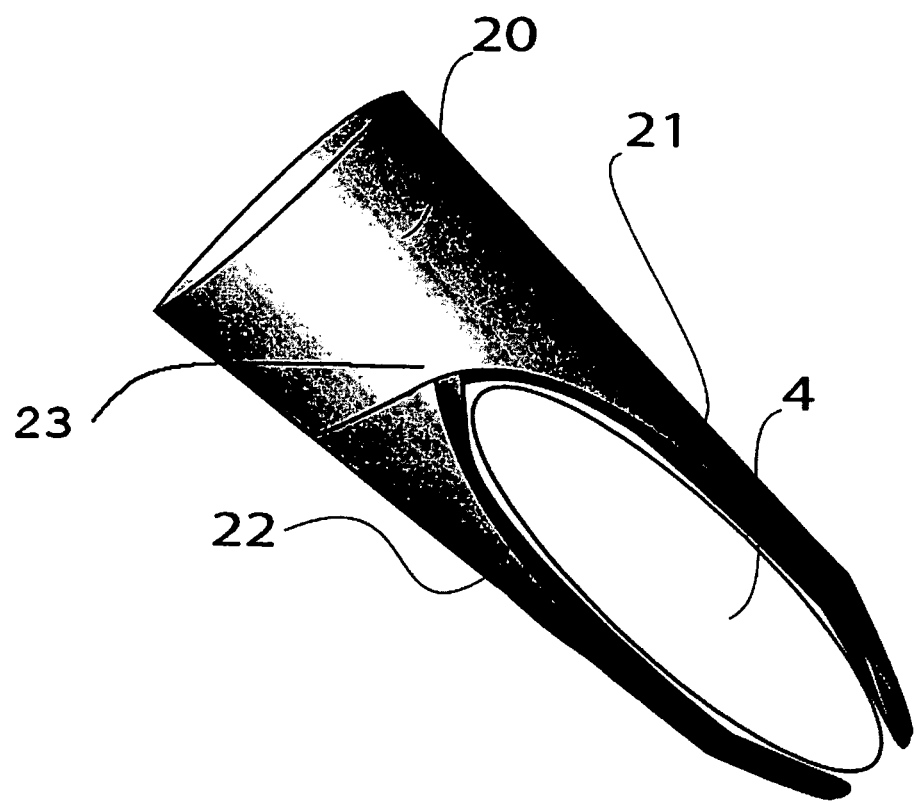
FIG. 6D is an enlarged view of the lamina with the laminar guards with an optional hinge design, fully advanced, demonstrating the safety stop preventing the advancement of the laminar guards into the spinal canal.
Figure 6E:
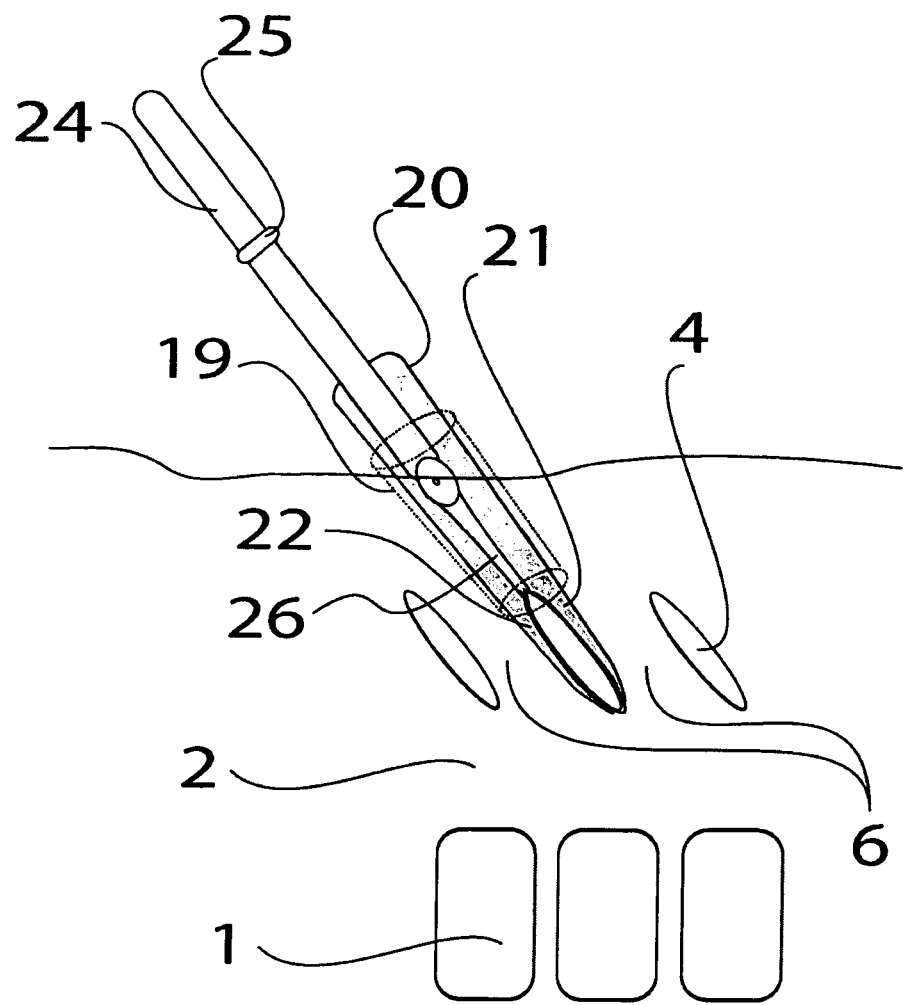
FIG. 6E is a lateral view of the patient showing the laminar guard having being advanced over the lamina, along the longitudinal axis of the lamina. A lamina dividing mechanism is positioned within the laminar guard.
Figure 6F:
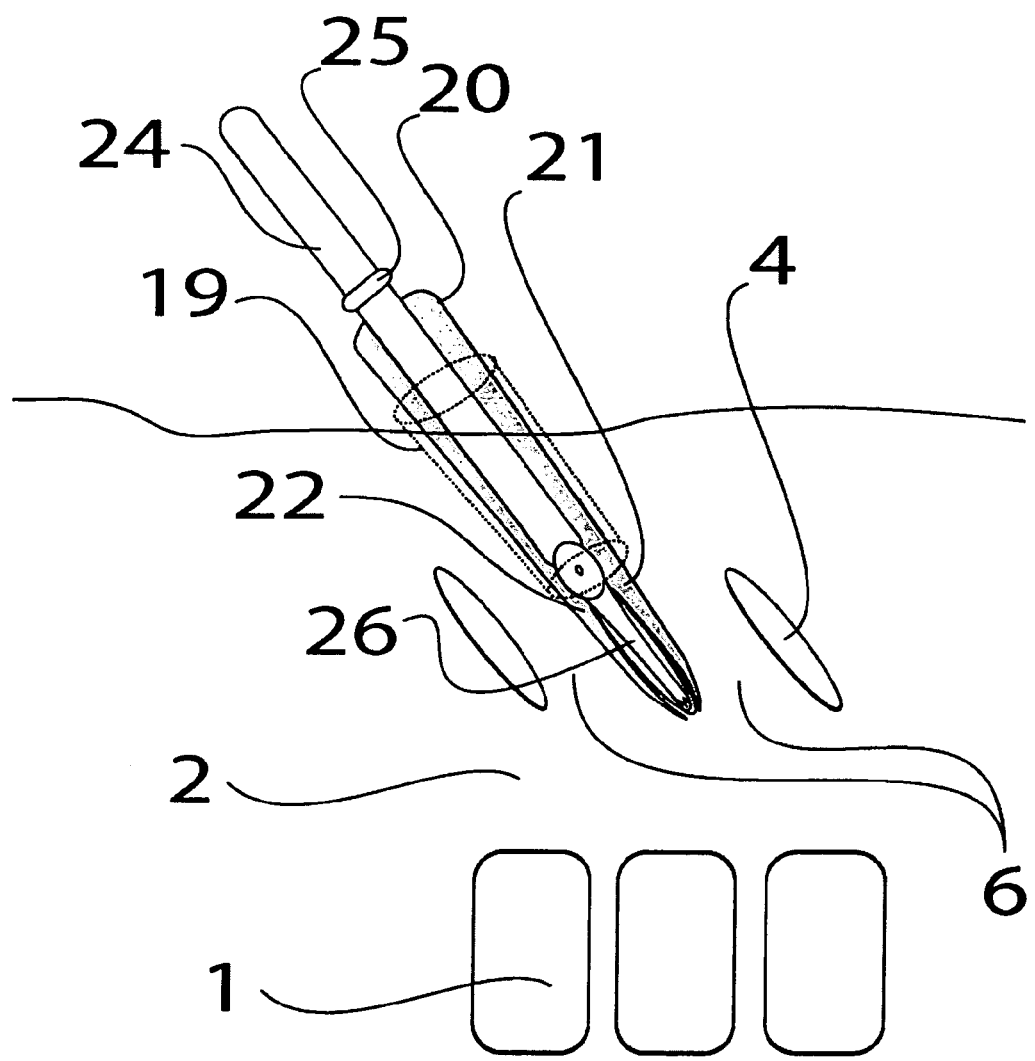
FIG. 6F is a lateral view of the patient showing the laminar guard having being advanced over the lamina, along the longitudinal axis of the lamina. The lamina dividing mechanism has been advanced dividing the lamina.
Figure 6G:
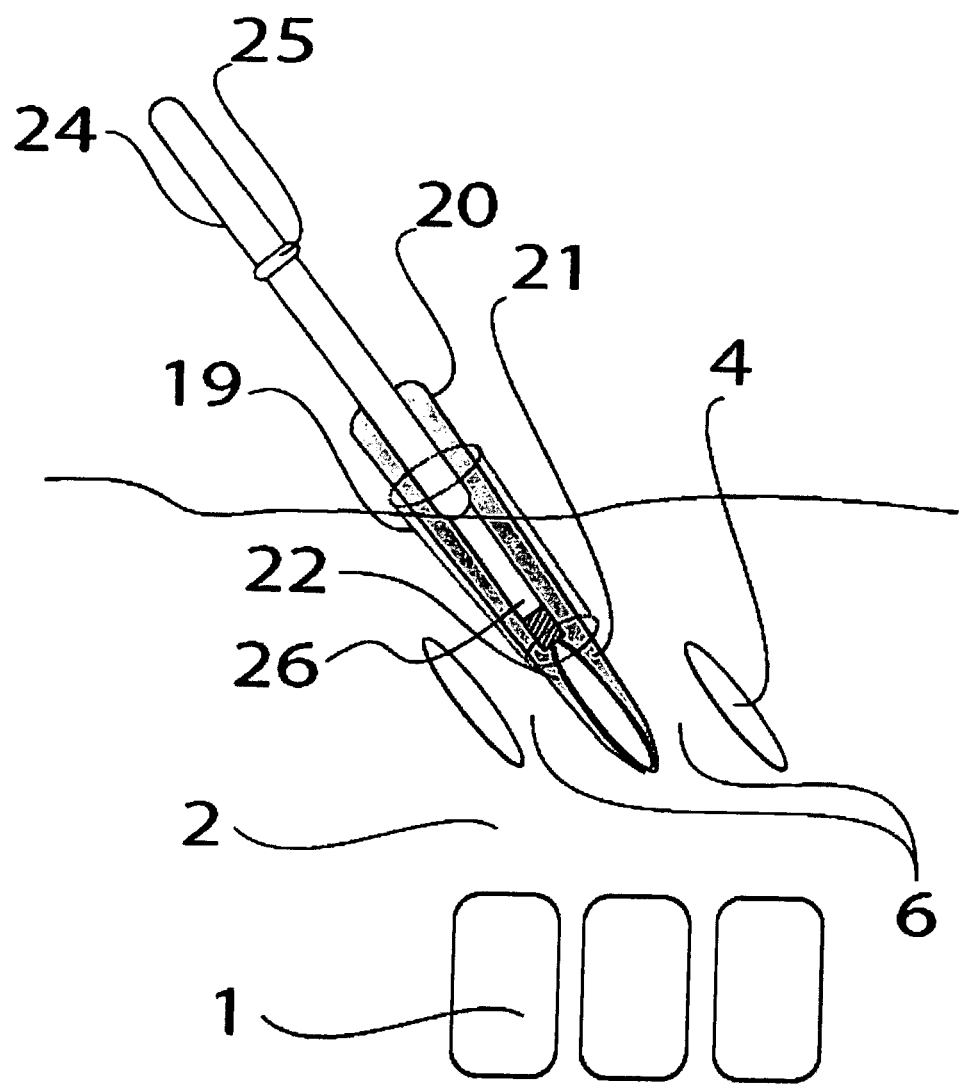
FIG. 6G is a lateral view of the patient showing the laminar guard having being advanced over the lamina, along the longitudinal axis of the lamina. The lamina dividing mechanism is positioned within the laminar guard.
Figure 6H:
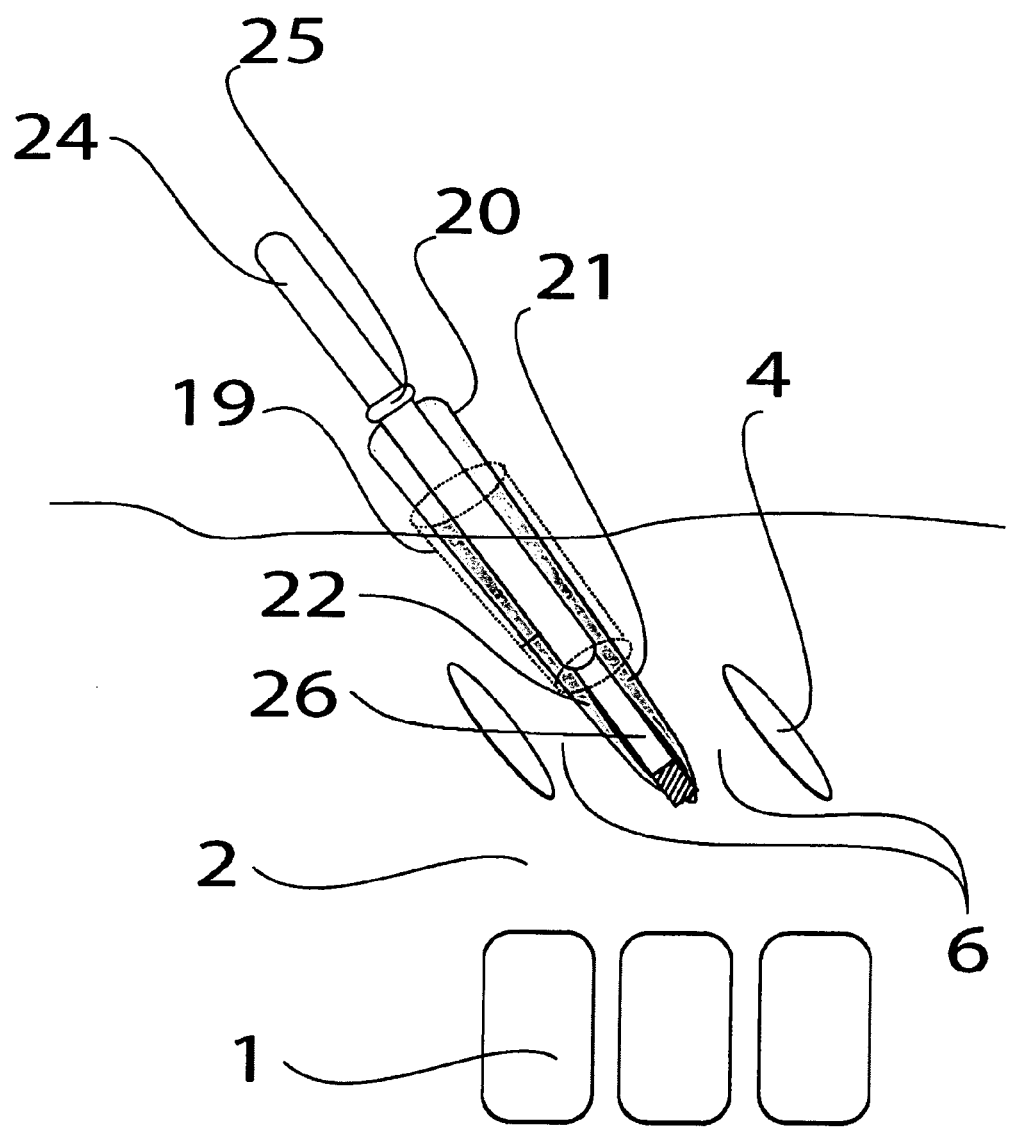
FIG. 6H is a lateral view of the patient showing the laminar guard having being advanced over the lamina, along the longitudinal axis of the lamina. The lamina dividing mechanism has been advanced dividing the lamina.

A dilator (19) or series of dilators is used to increase the size of the access pathway. These dilators can be supported by the instrument stabilizing apparatus. The laminar guards are connected to a cylindrical shaft 20, with a superior laminar guard 21, and an inferior laminar guard 22 extending from it. These guards are positioned in the inter laminar space superior and inferior to the lamina being treated, as shown in FIG. 6B. The laminar guards are advanced through the dilator (19) under image guidance. The sub (22) and supra (21) laminar guard walls surround the lamina (4) creating a safety stop that prevents the laminar guards from entering the spinal central canal (2) or the inter laminar space between the vertebrae (6) (FIGS. 6C and 6E). Once the laminar guards are securely fastened around the lamina, a saw, drill, burr, or other bone dividing mechanism (26) is lowered through the cylindrical shaft (20) until it reaches the lamina (4). The dividing mechanism (26) is then used to divide the lamina (4) (FIG. 6F). Based on the degree of stenosis or anatomy of the lamina, the laminar guard may need to be advanced stepwise under image guidance.

In another aspect of the invention, the distance to completely divide the lamina (4) can be measured and the size of the lamina dividing mechanism (26) and laminar guards (22 and 21) can be adjusted to the exact length of the lamina (4) to ensure that the lamina dividing mechanism (26) does not enter the spinal central canal (2) or the inter laminar space (6) (FIG. 6E-H).

The laminar guard can be advanced using imaging technology such as CT scan, MRI, X-ray, fluoroscopy or other guidance. Variable length laminar guards are available and the operator selects one based on measuring the longitudinal length of the lamina based on CT or other imaging study. The length of the sub- and supra-laminar guard walls matching the length of the lamina being worked on acts as a safety stop to prevent over advancement of the laminar guard into the spinal central canal (FIGS. 6C, 6D). The designs of two different variations of the laminar guard are shown in FIGS. 6C and 6D, with and without a hinge 23 or some other comparable mechanism for the guard to account for variability of the lamina width, based on the thickness of the lamina, anatomical location, or elasticity of the material used to manufacture the laminar guard. In a most preferred embodiment, the laminar guard is made of titanium.

A closer view of the lamina with the laminar guard fully advanced demonstrates the safety stop preventing the advancement of the laminar guard walls into the spinal canal (FIG. 6E). In this embodiment, the lamina dividing mechanism handle 24 with a security pin 25 is set to the appropriate length and is inserted into the cylindrical access shaft of the laminar guard. The lamina dividing mechanism can be seen positioned to divide the lamina along the lamina's longitudinal axis. Note in this embodiment that the saw blade or burr tip or other lamina dividing mechanism 26 length corresponds to the length of the lamina to act as an added safety. The blade's holding mechanism is wider than the saw blade and cannot advance past the border of the lamina that was divided, thereby preventing the saw blade from entering the spinal central canal (FIG. 6F). Use of an alternate dividing device such as a burr is demonstrated in FIGS. 6G and 6H.

Figure 6I:
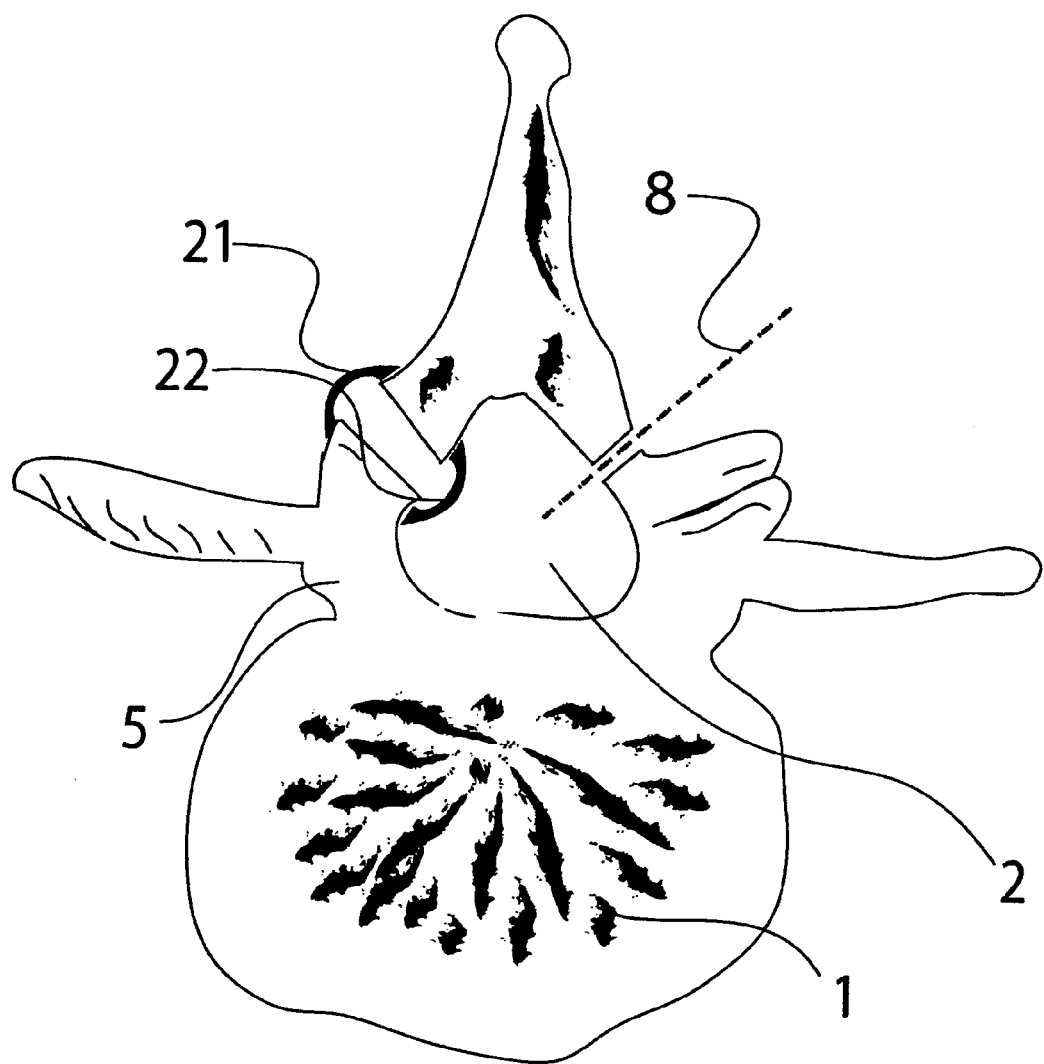
FIG. 6I is an axial view of vertebra showing the laminar guards in position on one lamina, and the lamina having already been divided on the other side of the vertebra.

The lamina dividing mechanism is advanced under image guidance dividing the lamina along its longitudinal axis. Note the saw length corresponds to the length of the lamina to act as added safety. The blade holding mechanism may be wider than the saw blade or burr tip, and cannot advance into the lamina that was divided, further preventing the saw blade from entering the spinal central canal. An axial view of vertebra, showing the laminar guard in position on one lamina and the other lamina having been divided, is shown in FIG. 6I.

Figure 7A:
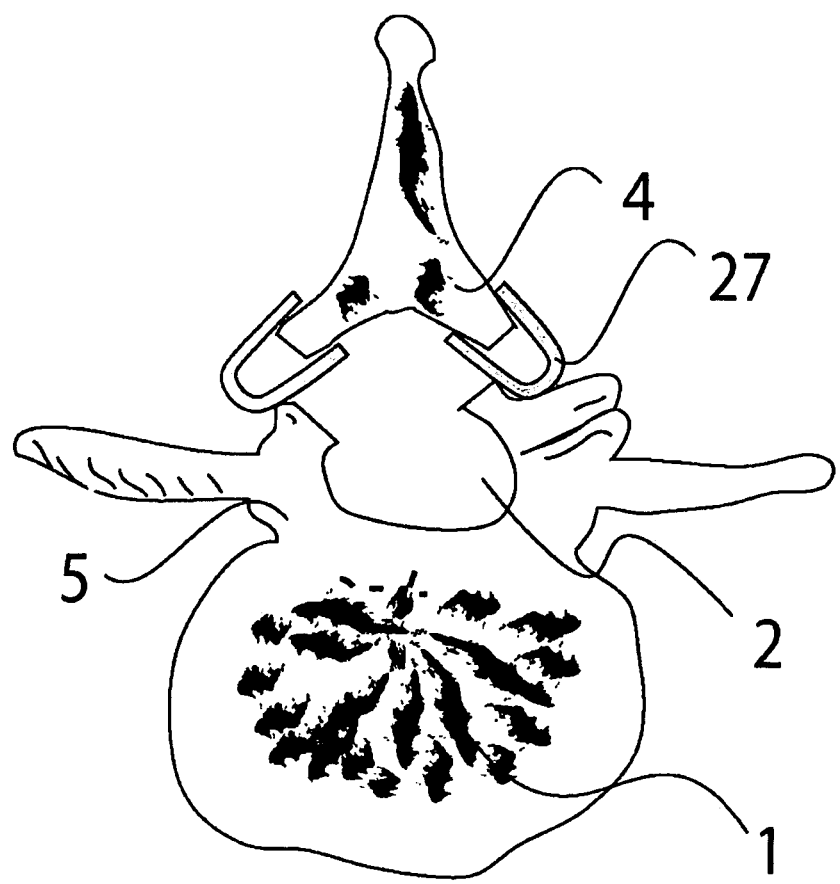
FIGS. 7A and 7B are axial views of the spine showing bilateral laminectomies having been performed, and clips (without and with teeth respectively) placed on the divided laminar edges to prevent the divided section of the vertebra from encroaching into the central canal space.
Figure 7B:
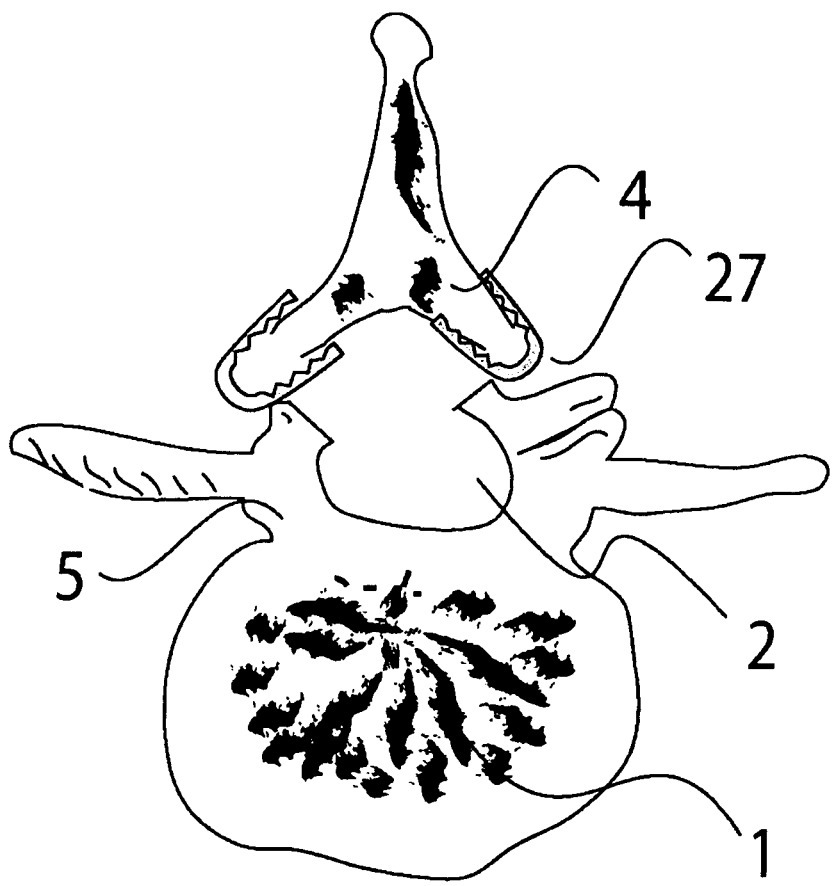

If bilateral laminar osteotomies are to be performed, the same approach is made to the contralateral lamina. During the dividing of the contralateral lamina, the laminar guards of the initial side are kept in position. Once both lamina have been divided, the laminar guards are rotated. The right guard may be rotated clockwise and the left guard may be rotated counter-clockwise. This process elevates the divided posterior elements of the vertebra, effectively expanding the central canal's posterior margin or "raising the roof" of the vertebra. With the posterior wall elevated, a laminar clip 27 is placed on the divided edge of the lamina. The laminar clip can either be placed on the segment of the lamina that has been elevated posteriorly or on the segment still attached to the pedicle (FIG. 7A). Alternatively, the clips may have teeth on the inner surface to help them achieve greater fixation to the laminar bone (FIG. 7B).

Figure 8:
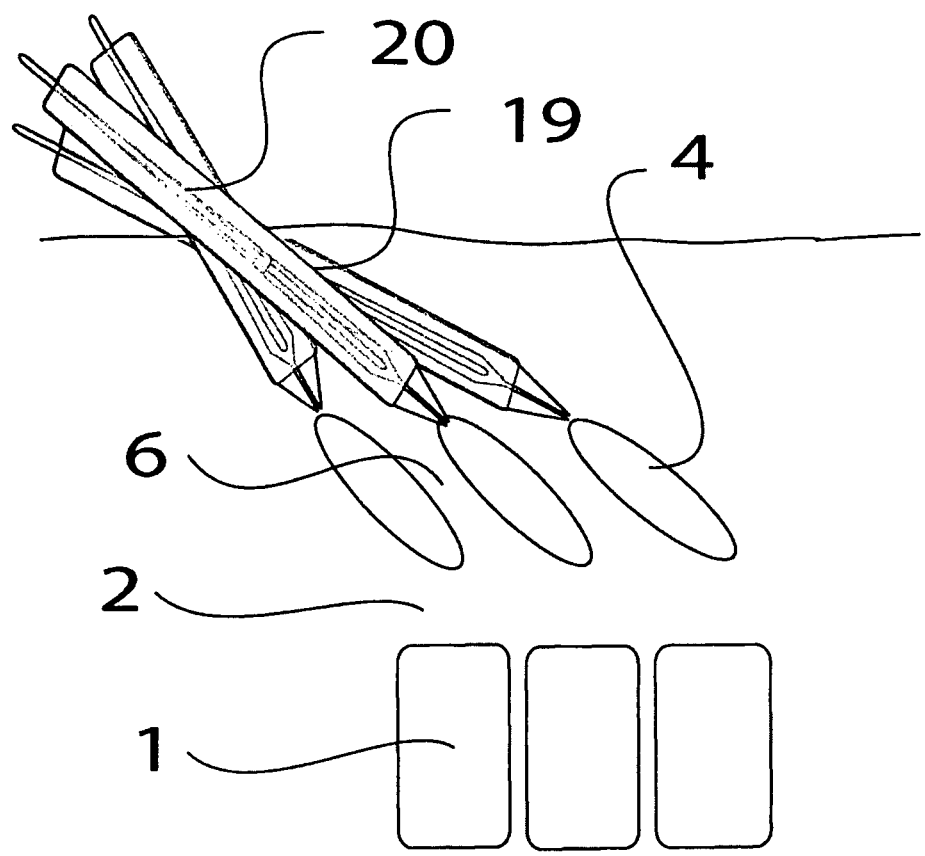
FIG. 8 is a lateral view of the patient showing the same skin incision being used to approach multiple laminas. Each lamina, however, is approached along its longitudinal axis.

FIG. 8 illustrates a lateral view of the patient showing multiple approaches to more than one lamina through the same skin incision by adjusting the angle of approach to the longitudinal laminar axes (FIG. 8). The ability to treat multiple laminas through a single small incision is of obvious benefit to both the patient and surgeon.

Figure 9:
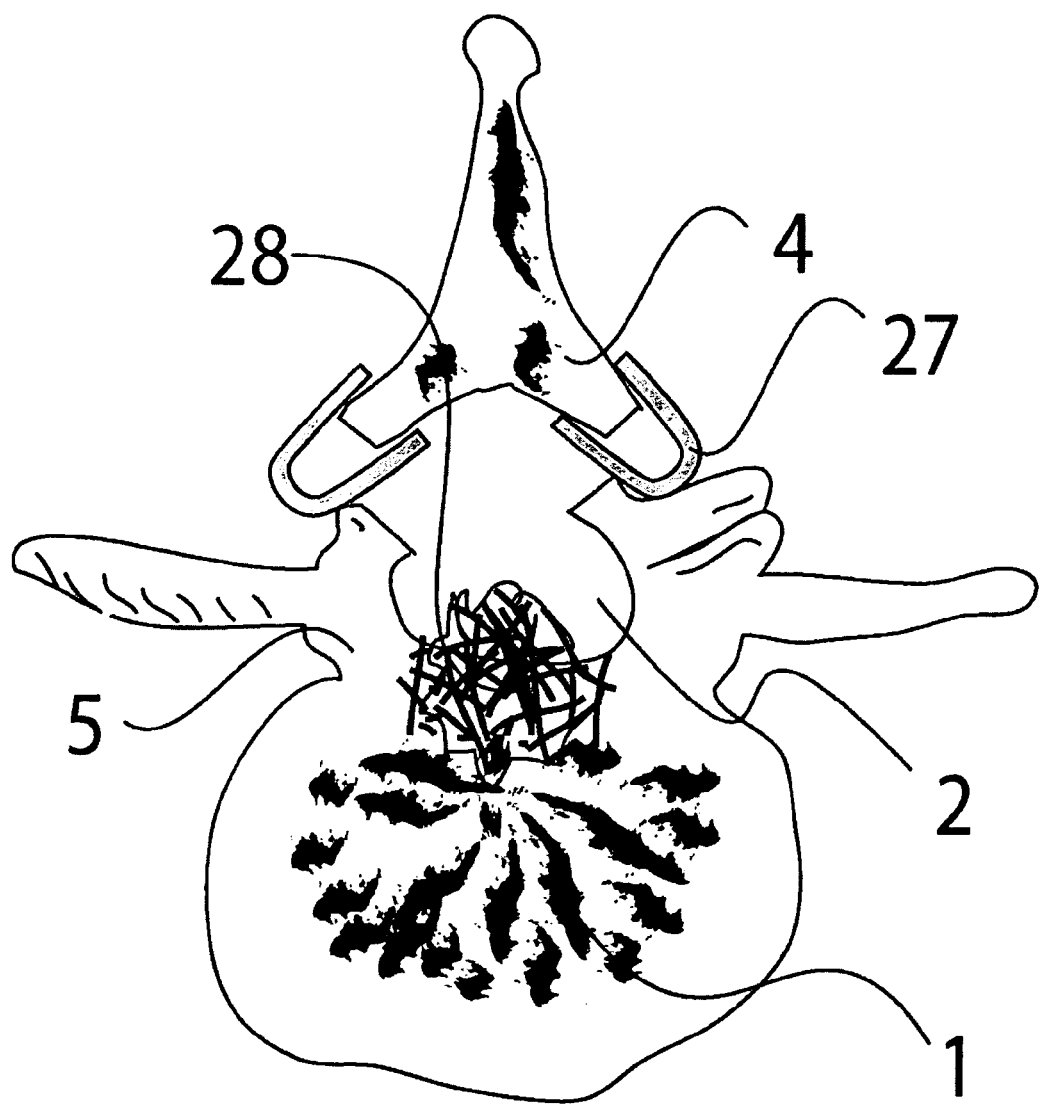
FIG. 9 is a cranial view of a spinal vertebrae with a burst fracture with displacement of the posterior wall or disc herniation into the spinal canal. Laminectomies have been performed to allow for decreased compression of the spinal cord or thecal sac during subsequent anterior spinal surgery.

FIG. 9 illustrates an axial view of a spinal vertebrae with a burst fracture 28. FIG. 9 illustrates displacement of the posterior wall within the canal with acute compression of the spinal cord, having been treated with bilateral laminar osteotomies as per the method contemplated by the invention. FIG. 9 also illustrates elevation of the posterior wall of the central canal.

Once the clips 27 have been placed, the site is irrigated and suctioned. Alternatively, an irrigation and suctioning system built into the procedure or device as contemplated by the present invention may be used during the entire process. In another aspect of the invention, osteo-inductive, osteo-conductive, or other bone healing material is placed on the divided laminar surface to aid in healing of the divided lamina.

In another aspect of the invention, a repeat CT scan is obtained to demonstrate the passage of the myelogram dye to the previous areas of stenosis. The CT scan can further demonstrate the increase in canal size and ensure that there is no dural leak or bleeding that is readily visualized. This control CT scan demonstrates that the procedure accomplished decompression of the spinal canal due to the spinal stenosis.

If the patient has spinal cord or thecal sac compression by the posterior aspects of the spinal canal, the above described procedure can be the performed as treatment.

Spinal decompression through a minimally invasive approach such as that contemplated by the present invention will shorten the length of time a patient spends in the hospital. There would be less blood loss and fewer wound healing complications.

Using a technique contemplated by the invention, decompression can be performed even in patients who are obese or otherwise have greater risk of complications with open surgery. The lamina dividing mechanism described herein cuts through the bone but not through soft tissue. This is a major benefit of this procedure. Additionally, the safeguards in place with the technique contemplated by the invention address safety concerns of the neuronal elements, including the thecal sac or the spinal cord.

Injection of contrast material prior to the procedure (myelography) will allow a better visualization of the nerve roots. This is another method by which to assure that the dural sac is not perforated during the procedure.

The above procedure can also be further performed in patients who are indicated for anterior spinal surgery either for discectomy and fusion, disc arthroplast, or other anterior procedure. There are added benefits of performing the above described procedure prior to anterior spinal surgery. For example, by increasing the spinal canal space allowing the neuronal elements to retract posteriorly, the surgeon would decrease the amount and possibility of pressure placed on the neuronal elements during anterior spinal surgery. This method significantly improves the safety margin for the patient. Thus, a technique contemplated by the invention would decrease the possible amount of cord compression during anterior spinal surgeries, such as anterior discectomies; fusions, or disk arthroplasty.

It will be apparent to those skilled in the art that various modifications and variations can be made in the present invention without departing from the spirit or scope of the invention. Thus, it is intended that the present invention covers the modifications and variations of this invention that come within the scope of any claims and their equivalents.

Although the invention has been described and illustrated with a certain degree of particularity, it is understood that the present disclosure has been made only by way of example, and that numerous changes in the conditions and order of steps can be resorted to by those skilled in the art without departing from the spirit and scope of the invention.

Index of Reference Numerals

1 VERTEBRAL BODY
2 CENTRAL CANAL
3 SPINOUS PROCESS
4 LAMINAE
5 PEDICULE
6 INTERLAMINAR SPACE
7 FACET JOINT
8 LONGITUDINAL AXIS
9 PERPENDICULAR AXIS
10 PATIENT
11 PROCEDURE TABLE
12 LAMINAR DIVIDING DEVICE
13 STAND
14 ARM
15 UNIVERSAL JOINT
16 CT-SCAN
17 OPERATOR
18 GUIDE WIRE
19 DILATOR
20 CYLINDRICAL SHAFT
21 SUPERIOR LAMINAR GUARD
22 INFERIOR LAMINAR GUARD
23 OPTIONAL HING IN LAMINER GAURD
24 LAMINA DIVIDING MECHANISM HANDLE
25 SECURITY PIN
26 LAMINA DIVIDING MECHANISM:
   SAW BLADE, BURR OR OTHER DIVIDING DEVICE
27 CLIP
28 FRACTURE OR HERNIATED DISK FRAGMENTS

What is claimed is:

1. A device for protecting a patient's sublaminar thecal sac and pari-laminar soft tissue structures while performing procedures on a spinal lamina of a patient, the spinal lamina having a longitudinal axis, said device being configured to be placed parallel to the longitudinal axis of the lamina and proximate to the lamina, and said device comprising:
   a sub-laminar wall and a supra-laminar wall, that converge at an inner surface at both a proximal end and a distal end of a tip, wherein the distal end of the device includes curved or angled leading outer surfaces configured to be convergent thus resulting in a tapering of the tip of the device, the converging sub-laminar and supra-laminar walls allowing the patient's lamina to be separated from the overlaying and underlying tissues; and
   a cannulate cylinder at least partially disposed above the supra-laminar and sub-laminar walls allowing access to the lamina with at least one of surgical tools, placement of devices, medications, or other therapeutic agents.

2. The device of claim 1, further comprising a lamina divider extendable within the cannulate cylinder along the longitudinal axis to engage the spinal lamina when the spinal lamina is received within the sub-laminar and supra-laminar walls.

3. The device of claim 1, wherein the sub-laminar wall and the supra-laminar wall form a bite at the free end of cannulate cylinder that defines a stop generally contoured to the shape of the spinal lamina to inhibit longitudinal movement of the cannulate cylinder.

4. The device of claim 1, wherein said device comprises at least one of a metal, a ceramic, a polymer, and a bioabsorbable material.

5. The device of claim 4, wherein said device comprises at least one of titanium and titanium alloy.

6. The device of claim 1 further comprising at least one of an irrigation system and a suction system.

7. The device of claim 1 further comprising at least one of a radio opaque marker, an radiolucent marker and an MRI marker.

8. The device of claim 1, wherein said device is adapted to accommodate at least one of surgical instruments and treatment instruments that can be used for dividing, drilling, burring, shaving, ablating or modifying of a patient's spinal lamina and surrounding boney and soft tissue structures.

9. The device of claim 1, wherein said device is used on at least one of a patient's cervical spine, thoracic spine, and lumbar spine.

10. The device of claim 1, wherein said device is used for separation of the underlying dura matter, other thecal sac, and sub-laminar tissues as well as overlaying pari-laminar tissue from the lamina.

11. The device of claim 1, wherein said device collects tissue debris and bone fragments created during performance of procedures.

12. The device of claim 1, wherein said device protects the patient's surrounding pari-laminar structures from breakage or failure of any surgical instrument used to perform the procedure.

13. The device of claim 1, wherein said device accommodates instrumentation of the lamina with clips or other surgical implantable devices.

14. The device of claim 1, wherein said device is inserted through the inter-laminar space.

15. The device of claim 1, wherein said sub- and super-laminar walls vary in length to prevent advancement of the device tip into the spinal central canal.

16. A device for protecting a patient's sublaminar thecal sac and pari-laminar soft tissue structures while performing procedures on a spinal lamina of the patient, the spinal lamina having a longitudinal axis, the device comprising:
   a hollow cannulate cylinder having a free end and a longitudinal axis parallel to the longitudinal axis of the spinal lamina when in use; and
   a sub-laminar wall and a supra-laminar wall, each wall extending from the free end of the cylindrical portion along the longitudinal axis, each wall having an inwardly curved tip spaced sufficiently apart from one another and having sufficient length along the longitudinal axis to receive the spinal lamina therebetween such that the sub-laminar wall separates the spinal lamina from underlying tissues and the supra-laminar wall separates the spinal lamina from overlaying tissues when the spinal lamina is received between the walls;
   wherein the sub-laminar wall and the supra-laminar wall are hingedly connected at a bite at the free end of the cannulate cylinder to allow for relative movement of the walls to receive the spinal lamina.

* * * * *